(12) United States Patent
Yu (10) Patent No.: US 8,979,050 B2
(45) Date of Patent: Mar. 17, 2015

(54) POSITIONING DEVICE FOR ROD (71) Applicant: Tsung-Yao Yu, Taichung (TW)

(72) Inventor: Tsung-Yao Yu, Taichung (TW)

(*) Notice: Subject to any disclaimer, the term of this patent is extended or adjusted under 35 U.S.C. 154(b) by 44 days.

(21) Appl. No.: 13/921,250

(22) Filed: Jun. 19, 2013

(65) Prior Publication Data
US 2014/0374557 A1 Dec. 25, 2014

(51) Int. Cl.
F16B 1/00 (2006.01)
F16B 2/06 (2006.01)
A47C 3/28 (2006.01)
A61B 19/00 (2006.01)

(52) U.S. Cl.
CPC ... *F16B 2/06* (2013.01); *A47C 3/28* (2013.01); *A61B 2019/268* (2013.01)
USPC ............ 248/230.2; 248/229.21; 248/227.3; 248/410; 248/412; 248/181.1; 403/90

(58) Field of Classification Search
CPC ...... A61B 2019/268; B25B 5/08; A47C 3/28; F16M 11/14
USPC ......... 248/230.2, 229.21, 227.3, 231.31, 410, 248/412, 181.1; 403/90; 24/535, 568, 536, 24/537, 540; 16/2.1
See application file for complete search history.

(56) References Cited

U.S. PATENT DOCUMENTS

| | | | | |
|---|---|---|---|---|
| 2,849,249 A * | 8/1958 | Fridolph | ................ | 403/376 |
| 4,115,966 A * | 9/1978 | DeLee | ................ | 52/148 |
| 5,903,645 A * | 5/1999 | Tsay | ................ | 379/455 |
| 6,142,699 A * | 11/2000 | Pao | ................ | 403/109.5 |
| 6,719,259 B2 * | 4/2004 | Huang et al. | ................ | 248/441.1 |
| 6,898,893 B1 * | 5/2005 | Mukdaprakorn | ................ | 43/21.2 |
| 7,179,200 B1 * | 2/2007 | Wu | ................ | 482/51 |
| 8,021,070 B2 * | 9/2011 | Bingham et al. | ................ | 403/109.5 |
| 8,257,231 B2 * | 9/2012 | Bingham et al. | ................ | 482/57 |
| 8,702,339 B2 * | 4/2014 | Ballentine | ................ | 403/322.4 |
| 2007/0252071 A1 * | 11/2007 | Huang | ................ | 248/539 |
| 2011/0280654 A1 * | 11/2011 | Bingham et al. | ................ | 403/374.5 |

* cited by examiner

*Primary Examiner* — Anita M King
(74) *Attorney, Agent, or Firm* — Alan Kamrath; Kamrath IP Lawfirm, P.A.

(57) ABSTRACT

A positioning device includes a base, a press board, an antislip piece, and a positioning unit. The base includes an opening, and a mounting space. The mounting space is mounted on a rod. The press board is slidably mounted in the opening. The antislip piece is mounted on the press board and is close to the mounting space. The antislip piece is made of elastic material and is softer than the press board. The positioning unit includes a shaft mounted on the base and a driving member rotatably and eccentrically connected with the shaft. The driving member is driven between a pressing position for locking the rod and a releasing position for unlocking the rod. Thus, the user only needs to drive the driving member to lock or unlock the rod so that the rod is locked or unlocked easily and quickly.

8 Claims, 6 Drawing Sheets

POSITIONING DEVICE FOR ROD

BACKGROUND OF THE INVENTION

1. Field of the Invention

The present invention relates to a positioning device and, more particularly, to a positioning device for a rod.

2. Description of the Related Art

Figure 1:
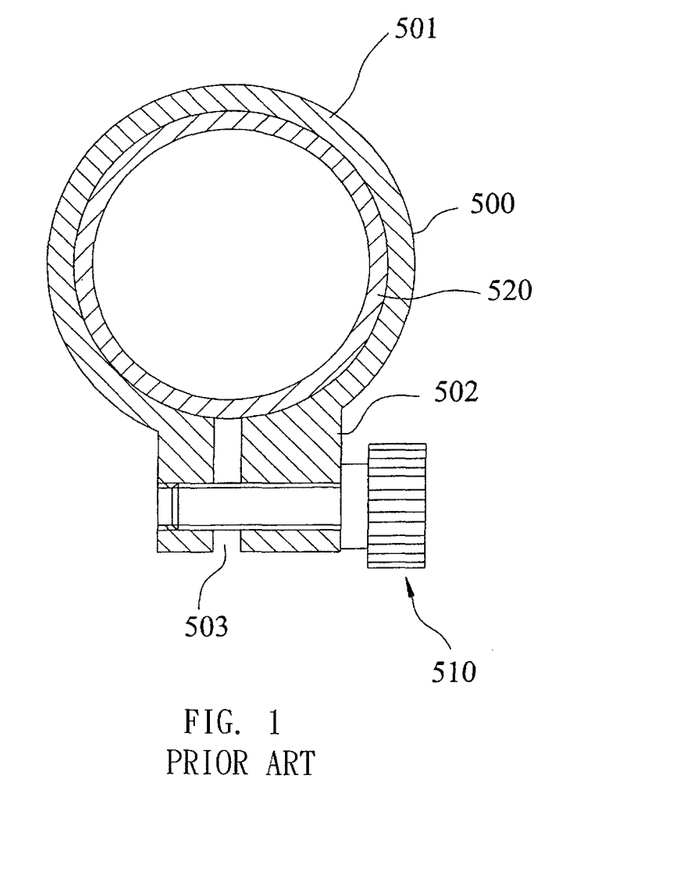
FIG. 1 is a cross-sectional view of a conventional positioning device for a rod in accordance with the prior art.

A conventional positioning device in accordance with the prior art shown in FIG. 1 is mounted on a rod 520 and comprises a clamping ring 500 and a bolt 510. The clamping ring 500 includes a C-shaped annular wall 501, two spaced fixing plates 502 mounted on two opposite ends of the annular wall 501, and a slit 503 defined between the fixing plates 502. The clamping ring 500 is mounted on the rod 520. Then, the bolt 510 is screwed through the fixing plates 502. When the bolt 510 is screwed tightly to reduce the width of the slit 503, the annular wall 501 of the clamping ring 500 presses the rod 520 so that the rod 520 is locked. When the bolt 510 is unscrewed to enlarge the width of the slit 503, the annular wall 501 of the clamping ring 500 releases the rod 520 so that the rod 520 is unlocked. However, the user has to screw the bolt 510 for locking the rod 520 and to unscrew the bolt 510 for unlocking the rod 520, thereby wasting the time and energy. In addition, the annular wall 501 of the clamping ring 500 easily produces an elastic fatigue during a long-term utilization so that the annular wall 501 of the clamping ring 500 cannot position the rod 520 exactly and closely. Further, the conventional positioning device is not assembled conveniently.

BRIEF SUMMARY OF THE INVENTION

The primary objective of the present invention is to provide a positioning device that can lock or unlock a rod conveniently to achieve energy saving and time saving functions.

In accordance with the present invention, there is provided a positioning device mounted on a rod, comprising a base, a press board, an antislip piece, and a positioning unit. The base includes an outer peripheral face, an inner peripheral face, an opening, and a sliding guide module. The inner peripheral face of the base defines a mounting space which is mounted on the rod. The opening of the base extends from the inner peripheral face to the outer peripheral face of the base. The sliding guide module of the base is located adjacent to the opening. The press board is slidably mounted in the opening of the base and is close to the mounting space of the base. The press board includes a guiding module which is slidable along the sliding guide module of the base. The antislip piece is mounted on and protruded outward from the press board. The antislip piece is close to the mounting space of the base. The antislip piece is made of elastic material and is softer than the press board. The positioning unit includes a shaft and a driving member. The shaft of the positioning unit is mounted on the base. The driving member of the positioning unit is rotatably and eccentrically connected with the shaft. The driving member of the positioning unit includes a pressing portion and a handle portion. The pressing portion of the driving member corresponds to the opening of the base. The handle portion of the driving member extends laterally from the pressing portion. The handle portion of the driving member is driven to move the pressing portion relative to the base between a pressing position and a releasing position. When the pressing portion of the driving member is moved to the pressing position, the pressing portion of the driving member presses the press board toward the rod to secure the rod. When the pressing portion of the driving member is moved to the releasing position, the pressing portion of the driving member releases the press board from the rod so that the rod is movable freely.

The base further includes two pivot plates spaced from each other. Each of the pivot plates of the base extends outward from the outer peripheral face of the base. The opening of the base is located between the pivot plates. One of the pivot plates of the base has a sliding face. The sliding guide module of the base includes at least one sliding guide portion formed in the sliding face. The guiding module of the press board includes at least one guiding portion slidable along the sliding guide portion of the sliding guide module. Preferably, the sliding guide portion of the sliding guide module is an elongate channel, and the guiding portion of the guiding module is a rail. The sliding guide module of the base further includes a plurality of first limit portions which are located at two opposite sides of the opening. The guiding module of the press board further includes a plurality of second limit portions secured on the first limit portions of the sliding guide module. Preferably, each of the first limit portions of the sliding guide module is a recess, and each of the second limit portions of the guiding module is a projection. The press board further includes a driven face and a fixing face. The driven face of the press board has an arc-shaped profile. The fixing face of the press board is located opposite to the driven face. The antislip piece is secured in the press board and corresponds to the fixing face of the press board. The pressing portion of the driving member presses the driven face of the press board. The pressing portion of the driving member has an arc-shaped profile. The guiding module of the press board has a bottom side provided with at least one oblique face. The oblique face of the guiding module is extended from the fixing face of the press board toward the driven face of the press board and is gradually deflected downward.

According to the primary advantage of the present invention, the user only needs to drive the driving member to lock or unlock the rod so that the rod is locked or unlocked easily and quickly.

According to another advantage of the present invention, the press board and the antislip piece clamps the rod the pressing position so that the rod is locked tightly and closely.

According to a further advantage of the present invention, the antislip piece is sandwiched between the rod and the press board so that the press board will not directly contact the rod and will not be deformed or distorted during a long-term utilization.

Further benefits and advantages of the present invention will become apparent after a careful reading of the detailed description with appropriate reference to the accompanying drawings.

DETAILED DESCRIPTION OF THE INVENTION

Referring to the drawings and initially to FIGS. 2-5, a positioning device in accordance with the preferred embodiment of the present invention is used to position a bearing unit 70 which is used for placing a tablet personal computer 80 and the like. The bearing unit 70 includes a support seat 702, a connector 703, and an upright rod 701. The tablet personal computer 80 is placed on the support seat 702 of the bearing unit 70. The connector 703 of the bearing unit 70 protrudes outward from the back face of the support seat 702. The positioning device is mounted on the rod 701 of the bearing unit 70 and is pivotally connected with the connector 703 of the bearing unit 70.

The positioning device comprises a base 1, a press board 2, an antislip piece 4, and a positioning unit 3.

The base 1 includes an outer peripheral face 11, an inner peripheral face 12, an opening 13, and a sliding guide module 10. The inner peripheral face 12 of the base 1 defines a mounting space 121 which is mounted on the rod 701. The opening 13 of the base 1 extends from the inner peripheral face 12 to the outer peripheral face 11 of the base 1 and is connected to the mounting space 121. The sliding guide module 10 of the base 1 is located adjacent to the opening 13. The base 1 further includes two pivot plates 14 spaced from each other, and a coupling portion 16 pivotally connected with the connector 703 of the bearing unit 70. Each of the pivot plates 14 of the base 1 extends outward from the outer peripheral face 11 of the base 1. The opening 13 of the base 1 is located between the pivot plates 14. One of the pivot plates 14 of the base 1 has a sliding face 141 which is located adjacent to the opening 13. The sliding guide module 10 of the base 1 includes at least one sliding guide portion 142 formed in the sliding face 141. The sliding guide module 10 of the base 1 further includes a plurality of first limit portions 15 which are located at two opposite sides of the opening 13. The first limit portions 15 of the sliding guide module 10 are located between the pivot plates 14 of the base 1.

The press board 2 is slidably mounted in the opening 13 of the base 1 and is close to the mounting space 121 of the base 1. The press board 2 includes a guiding module 20 which is slidable along the sliding guide module 10 of the base 1. The guiding module 20 of the press board 2 includes at least one guiding portion 21 slidable along the sliding guide portion 142 of the sliding guide module 10. Preferably, the sliding guide portion 142 of the sliding guide module 10 is an elongate channel, and the guiding portion 21 of the guiding module 20 is a rail. The guiding portion 21 of the guiding module 20 has an oblique face 211 corresponding to a bottom face of the sliding guide portion 142 of the sliding guide module 10. The guiding module 20 of the press board 2 further includes a plurality of second limit portions 22 secured on the first limit portions 15 of the sliding guide module 10. Preferably, each of the first limit portions 15 of the sliding guide module 10 is a recess, and each of the second limit portions 22 of the guiding module 20 is a projection. In the preferred embodiment of the present invention, the sliding guide module 10 of the base 1 includes two sliding guide portions 142 and four first limit portions 15, and the guiding module 20 of the press board 2 includes two guiding portions 21 and four second limit portions 22. The press board 2 further includes a driven face 23 and a fixing face 24. The driven face 23 of the press board 2 has an arc-shaped profile. The fixing face 24 of the press board 2 is located opposite to the driven face 23.

The antislip piece 4 is mounted on and protruded outward from the press board 2. The antislip piece 4 is close to the mounting space 121 of the base 1. The antislip piece 4 is made of elastic material, such as rubber, and is softer than the press board 2. The antislip piece 4 is secured in the press board 2 and corresponds to the fixing face 24 of the press board 2.

The positioning unit 3 includes a shaft 31 and a driving member 32. The shaft 31 of the positioning unit 3 is mounted on the base 1. The driving member 32 of the positioning unit 3 is rotatably and eccentrically connected with the shaft 31. The driving member 32 of the positioning unit 3 includes a pressing portion 321 and a handle portion 322. The pressing portion 321 of the driving member 32 corresponds to the opening 13 of the base 1 and has an arc-shaped profile. The pressing portion 321 of the driving member 32 presses the driven face 23 of the press board 2. The handle portion 322 of the driving member 32 extends laterally from the pressing portion 321. The handle portion 322 of the driving member 32 is driven to move the pressing portion 321 relative to the base 1 between a pressing position and a releasing position. When the pressing portion 321 of the driving member 32 is moved to the pressing position, the pressing portion 321 of the driving member 32 presses the press board 2 toward the rod 701 to secure the rod 701. When the pressing portion 321 of the driving member 32 is moved to the releasing position, the pressing portion 321 of the driving member 32 releases the press board 2 from the rod 701 to make the rod 701 move freely.

Figure 2:
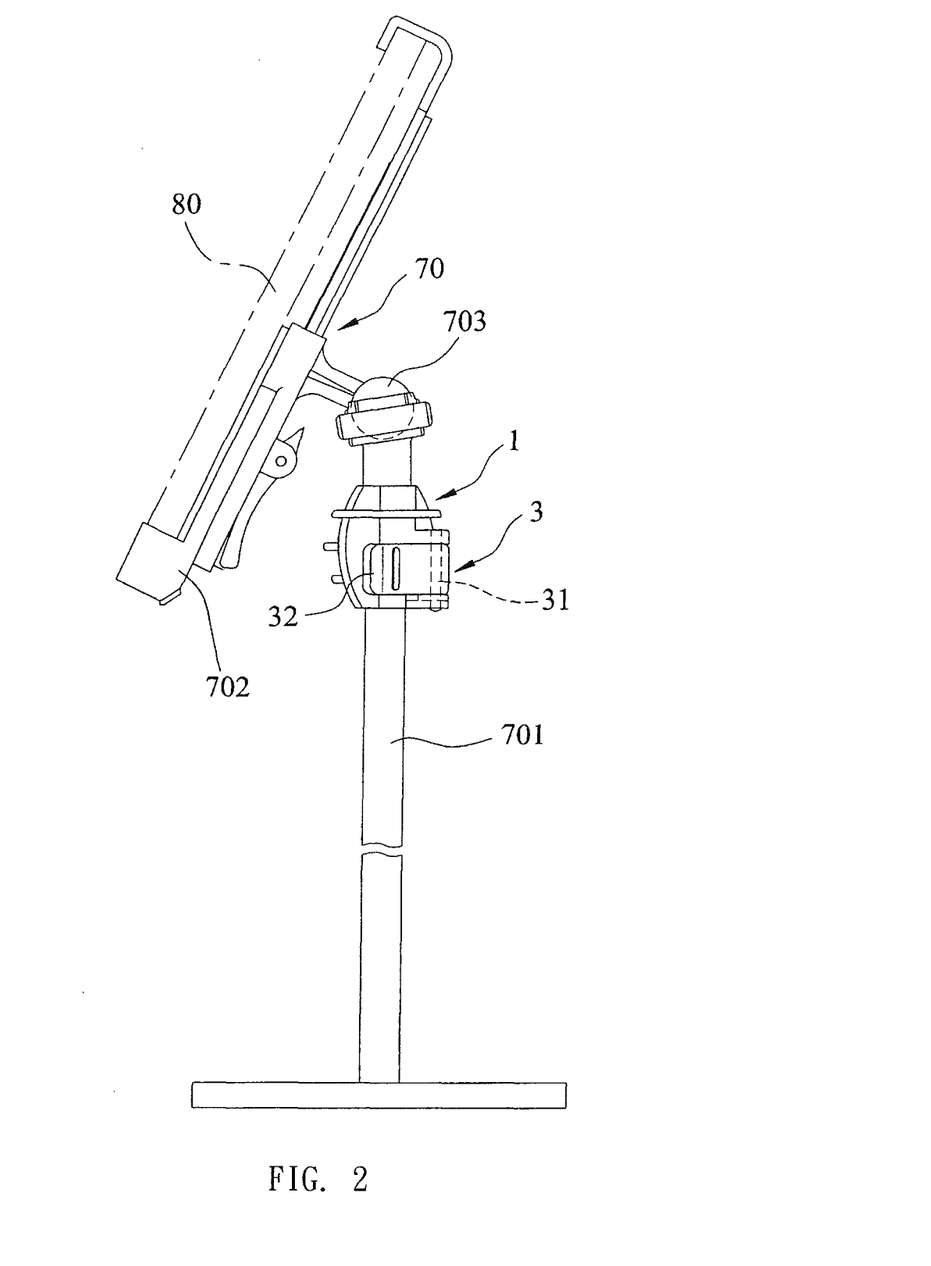
FIG. 2 is a schematic side view of a positioning device for a rod in accordance with the preferred embodiment of the present invention.
Figure 3:
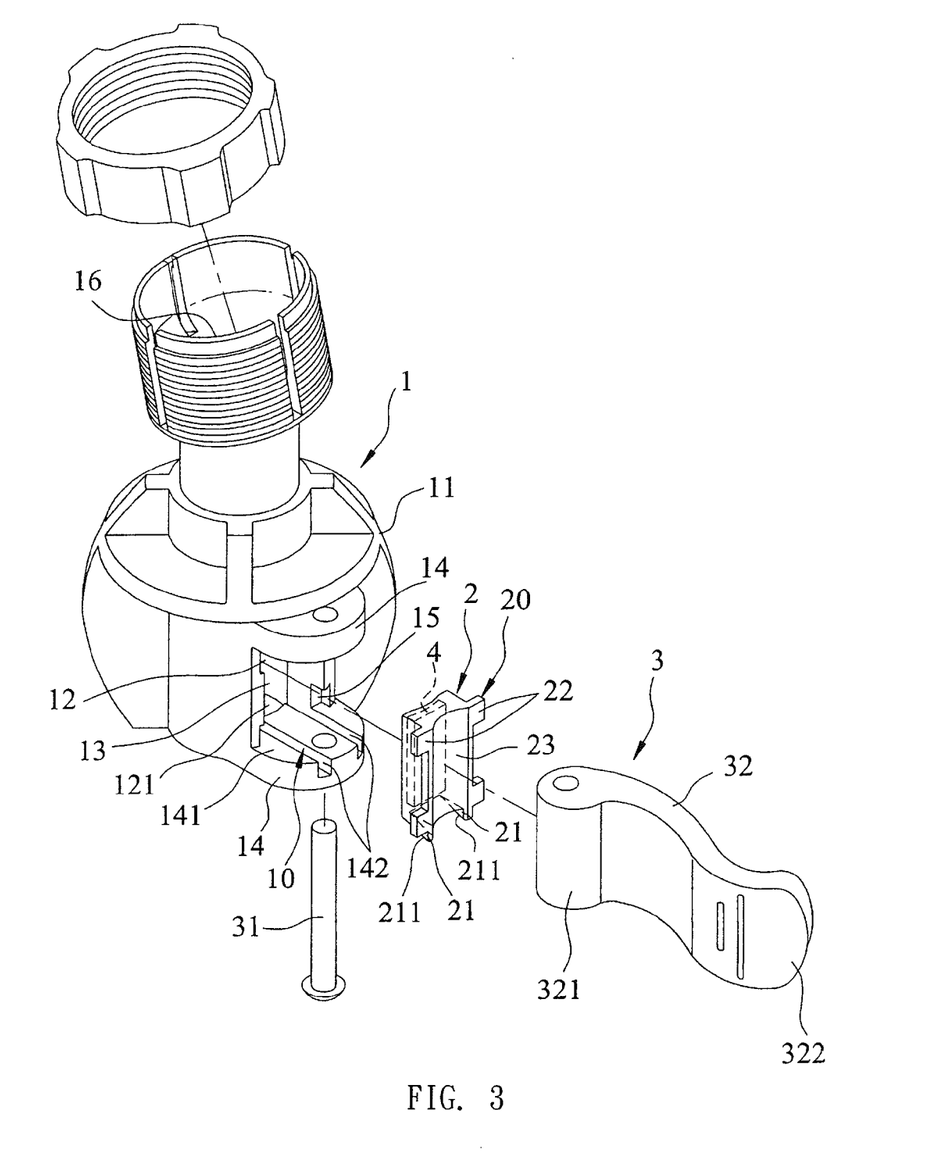
FIG. 3 is a partially exploded perspective view of the positioning device for a rod as shown in FIG. 2.
Figure 4:
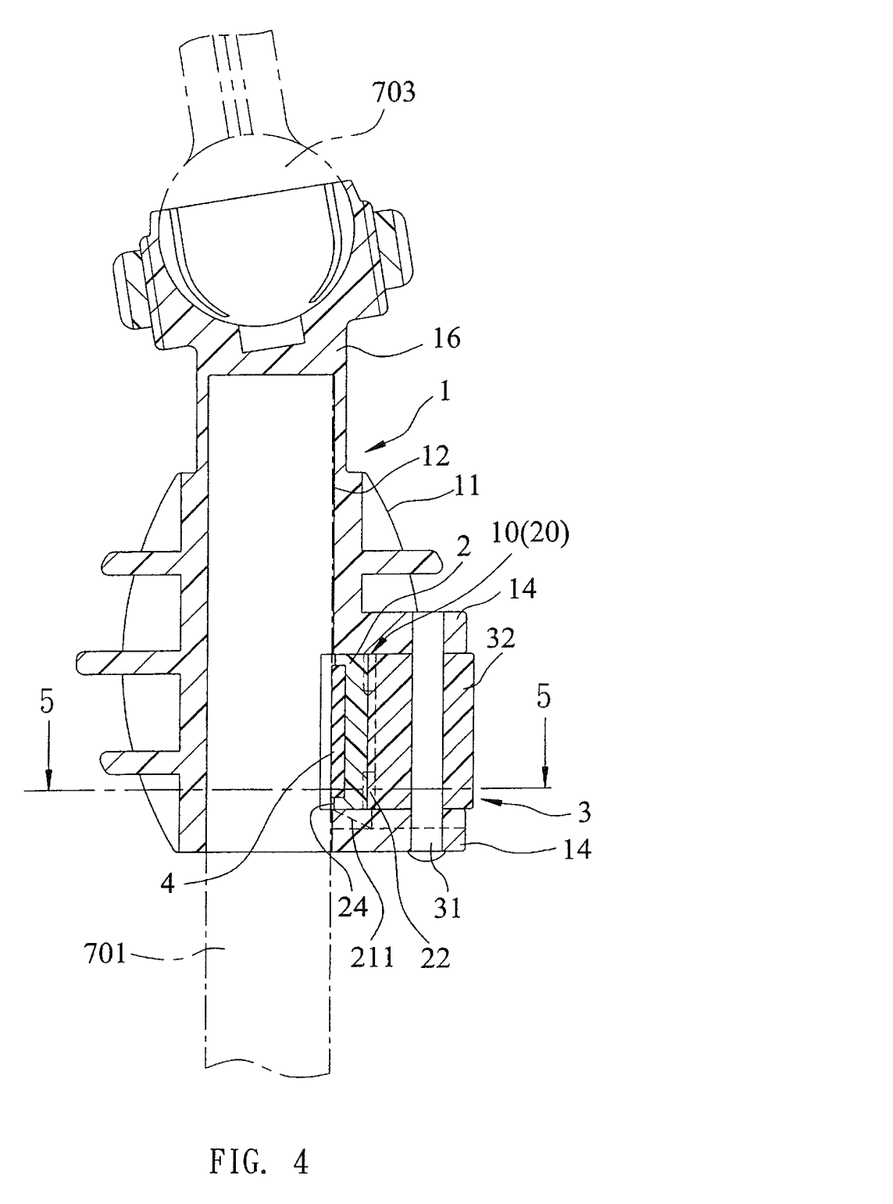
FIG. 4 is a cross-sectional view of the positioning device for a rod as shown in FIG. 2.
Figure 5:
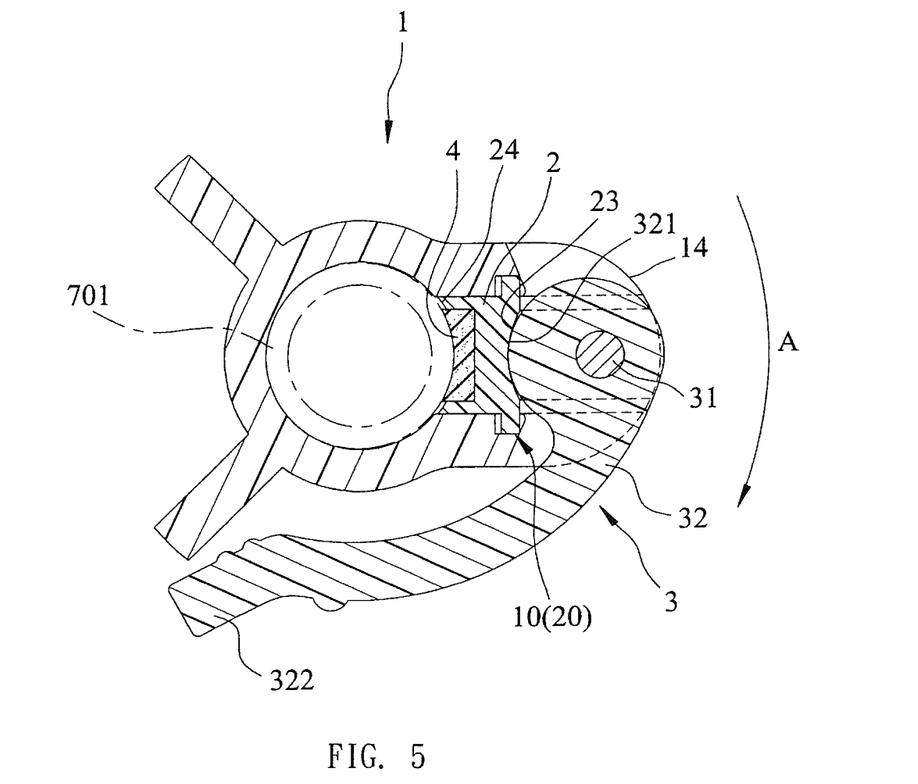
FIG. 5 is a cross-sectional view of the positioning device for a rod taken along line 5-5 as shown in FIG. 4, showing the pressing portion of the driving member is disposed at the pressing position.
Figure 6:
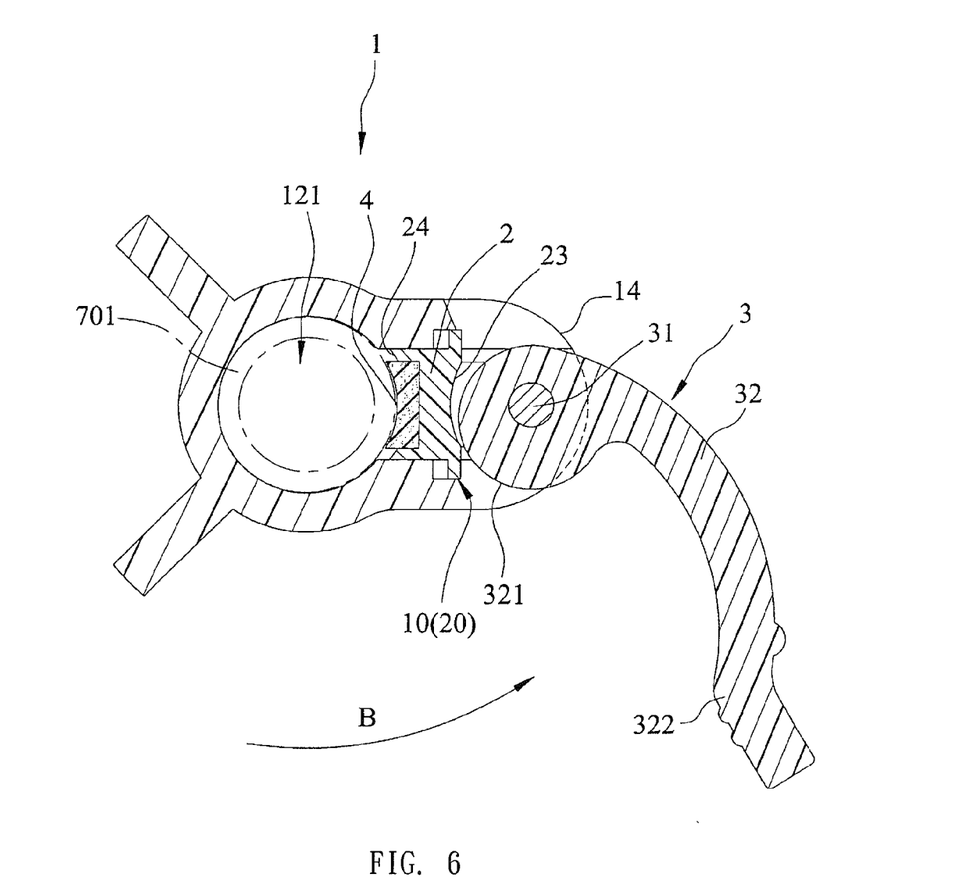
FIG. 6 is a schematic operational view of the positioning device for a rod as shown in FIG. 5, showing the pressing portion of the driving member is disposed at the releasing position.

In operation, referring to FIGS. 5 and 6 with reference to FIGS. 2-4, when the handle portion 322 of the driving member 32 is driven in the clockwise direction indicated by an arrow "A" as shown in FIG. 5, the pressing portion 321 of the driving member 32 is moved toward the driven face 23 of the press board 2 by the eccentric arrangement of the pressing portion 321 of the driving member 32 relative to the shaft 31. When the pressing portion 321 of the driving member 32 abuts the driven face 23 of the press board 2, the driving member 32 reaches the pressing position. When the pressing portion 321 of the driving member 32 is moved to the pressing position, the pressing portion 321 of the driving member 32 presses the press board 2 toward the rod 701 of the bearing unit 70 so that the antislip piece 4 clamps the rod 701 of the bearing unit 70 to position the rod 701 of the bearing unit 70 in place. At this time, the pressing portion 321 of the driving member 32 has an arc-shaped profile, and the driven face 23 of the press board 2 also has an arc-shaped profile to match the pressing portion 321 of the driving member 32, to increase the contact area between the driven face 23 of the press board 2 and the pressing portion 321 of the driving member 32, so that the antislip piece 4 clamps the rod 701 of the bearing unit 70 exactly. In addition, the antislip piece 4 is made of elastic material with an antislip function so that the antislip piece 4 clamps the rod 701 of the bearing unit 70 tightly and closely. In addition, the antislip piece 4 is sandwiched between the rod 701 of the bearing unit 70 and the press board 2 so that the press board 2 will not directly contact the rod 701 of the bearing unit 70 and will not be deformed or distorted during a long-term utilization.

On the contrary, when the handle portion 322 of the driving member 32 is driven in the counterclockwise direction indicated by an arrow "B" as shown in FIG. 6, the pressing portion 321 of the driving member 32 is moved to space from the driven face 23 of the press board 2 by the eccentric arrangement of the pressing portion 321 of the driving member 32 relative to the shaft 31. When the pressing portion 321 of the driving member 32 is detached from the driven face 23 of the press board 2, the driving member 32 reaches the releasing position. When the pressing portion 321 of the driving member 32 is moved to the releasing position, the pressing portion 321 of the driving member 32 releases the press board 2 which release the antislip piece 4 from the rod 701 of the bearing unit 70 so that the rod 701 of the bearing unit 70 is unlocked from the antislip piece 4 and is moved freely in the mounting space 121 of the base 1.

It is to be noted that, when the rod 701 of the bearing unit 70 is externally inserted into the mounting space 121 of the base 1, the oblique face 211 of the guiding portion 21 guides movement of the rod 701 so that the rod 701 of the bearing unit 70 is introduced into the mounting space 121 of the base 1 easily and conveniently by guidance of the oblique face 211, and will not be blocked by the press board 2 during movement.

It is appreciated that, the second limit portions 22 of the guiding module 20 are secured on the first limit portions 15 of the sliding guide module 10 to locate the press board 2 between the pivot plates 14 of the base 1, so that the press board 2 is positioned in the base 1 solidly and stably and will not fall into the mounting space 121 of the base 1.

Accordingly, the user only needs to drive the driving member 32 to lock or unlock the rod 701 so that the rod 701 is locked or unlocked easily and quickly. In addition, the press board 2 and the antislip piece 4 clamps the rod 701 the pressing position so that the rod 701 is locked tightly and closely. Further, the antislip piece 4 is sandwiched between the rod 701 and the press board 2 so that the press board 2 will not directly contact the rod 701 and will not be deformed or distorted during a long-term utilization to enhance the structural strength of the positioning device.

Although the invention has been explained in relation to its preferred embodiment(s) as mentioned above, it is to be understood that many other possible modifications and variations can be made without departing from the scope of the present invention. It is, therefore, contemplated that the appended claim or claims will cover such modifications and variations that fall within the true scope of the invention.

The invention claimed is:

1. A positioning device mounted on a rod, comprising:
a base, a press board, an antislip piece, and a positioning unit, wherein:
the base includes an outer peripheral face, an inner peripheral face, an opening, and a sliding guide module;
the inner peripheral face of the base defines a mounting space which is mounted on the rod;
the opening of the base extends from the inner peripheral face to the outer peripheral face of the base;
the sliding guide module of the base is located adjacent to the opening;
the press board is slidably mounted in the opening of the base and is close to the mounting space of the base;
the press board includes a guiding module which is slidable along the sliding guide module of the base;
the antislip piece is mounted on and protruded outward from the press board;
the antislip piece is close to the mounting space of the base;
the antislip piece is made of elastic material and is softer than the press board;
the positioning unit includes a shaft and a driving member;
the shaft of the positioning unit is mounted on the base;
the driving member of the positioning unit is rotatable and eccentrically connected with the shaft;
the driving member of the positioning unit includes a pressing portion and a handle portion;
the pressing portion of the driving member corresponds to the opening of the base;
the handle portion of the driving member extends laterally from the pressing portion;
the handle portion of the driving member is driven to move the pressing portion relative to the base between a pressing position and a releasing position;
when the pressing portion of the driving member is moved to the pressing position, the pressing portion of the driving member presses the press board toward the rod to secure the rod;
when the pressing portion of the driving member is moved to the releasing position, the pressing portion of the driving member releases the press board from the rod so that the rod is movable freely;
the base further includes two pivot plates spaced from each other;
each of the two pivot plates of the base extends outward from the outer peripheral face of the base;
the opening of the base is located between the two pivot plates;
one of the two pivot plates of the base has a sliding face;
the sliding guide module of the base includes at least one sliding guide portion formed in the sliding face;
the guiding module of the press board includes at least one guiding portion slidable along the at least one sliding guide portion of the sliding guide module;
the at least one sliding guide portion of the sliding guide module is an elongate channel; and
the at least one guiding portion of the guiding module is a rail.

2. The positioning device of claim 1, wherein:
the sliding guide module of the base further includes a plurality of first limit portions which are located at two opposite sides of the opening; and
the guiding module of the press board further includes a plurality of second limit portions secured on the plurality of first limit portions of the sliding guide module.

3. The positioning device of claim 2, wherein:
each of the plurality of first limit portions of the sliding guide module is a recess; and
each of the plurality of second limit portions of the guiding module is a projection.

4. The positioning device of claim 3, wherein:
the press board further includes a driven face and a fixing face;
the driven face of the press board has an arc-shaped profile;
the fixing face of the press board is located opposite to the driven face;
the antislip piece is secured in the press board and corresponds to the fixing face of the press board;
the pressing portion of the driving member presses the driven face of the press board; and
the pressing portion of the driving member has an arc-shaped profile.

5. A positioning device mounted on a rod, comprising:
a base, a press board, an antislip piece, and a positioning unit, wherein:
the base includes an outer peripheral face, an inner peripheral face, an opening, and a sliding guide module;
the inner peripheral face of the base defines a mounting space which is mounted on the rod;
the opening of the base extends from the inner peripheral face to the outer peripheral face of the base;
the sliding guide module of the base is located adjacent to the opening;

the press board is slidably mounted in the opening of the base and is close to the mounting space of the base;

the press board includes a guiding module which is slidable along the sliding guide module of the base;

the antislip piece is mounted on and protruded outward from the press board;

the antislip piece is close to the mounting space of the base;

the antislip piece is made of elastic material and is softer than the press board;

the positioning unit includes a shaft and a driving member;

the shaft of the positioning unit is mounted on the base;

the driving member of the positioning unit is rotatably and eccentrically connected with the shaft;

the driving member of the positioning unit includes a pressing portion and a handle portion;

the pressing portion of the driving member corresponds to the opening of the base;

the handle portion of the driving member extends laterally from the pressing portion;

the handle portion of the driving member is driven to move the pressing portion relative to the base between a pressing position and a releasing position;

when the pressing portion of the driving member is moved to the pressing position, the pressing portion of the driving member presses the press board toward the rod to secure the rod;

when the pressing portion of the driving member is moved to the releasing position, the pressing portion of the driving member releases the press board from the rod so that the rod is movable freely; and the guiding module of the press board has a bottom side provided with at least one oblique face.

6. The positioning device of claim 5, wherein:

the base further includes two pivot plates spaced from each other;

each of the two pivot plates of the base extends outward from the outer peripheral face of the base; and the opening of the base is located between the two pivot plates.

7. The positioning device of claim 6, wherein:

one of the two pivot plates of the base has a sliding face;

the sliding guide module of the base includes at least one sliding guide portion formed in the sliding face; and the guiding module of the press board includes at least one guiding portion slidable along the sliding guide portion of the at least one sliding guide module.

8. The positioning device of claim 5, wherein:

the press board further includes a driven face and a fixing face;

the fixing face of the press board is located opposite to the driven face;

the pressing portion of the driving member presses the driven face of the press board; and the at least one oblique face of the guiding module is extended from the fixing face of the press board toward the driven face of the press board and is gradually deflected downward.

* * * * *